United States Patent [19]

Nelson et al.

[11] Patent Number: 5,223,261

[45] Date of Patent: Jun. 29, 1993

[54] TRANSDERMAL ESTRADIOL DELIVERY SYSTEM

[75] Inventors: Gregory R. Nelson; Horst-Georg Zerbe; Cheryl L. Moore; Steven M. Wick, all of St. Paul, Minn.

[73] Assignee: Riker Laboratories, Inc., St. Paul, Minn.

[21] Appl. No.: 815,908

[22] Filed: Dec. 31, 1991

Related U.S. Application Data

[63] Continuation of Ser. No. 398,168, Aug. 24, 1989, abandoned, which is a continuation-in-part of Ser. No. 322,895, Mar. 10, 1989, abandoned, which is a continuation-in-part of Ser. No. 160,635, Feb. 26, 1988, abandoned.

[51] Int. Cl.$^5$ ............................................. A61F 13/00
[52] U.S. Cl. .................................... 424/443; 424/448; 424/447; 424/449
[58] Field of Search ........................ 424/447, 448, 449

[56] References Cited

U.S. PATENT DOCUMENTS

| | | | |
|---|---|---|---|
| 3,598,122 | 8/1971 | Zaffaroni | 424/449 |
| 3,598,123 | 8/1971 | Zaffaroni | 424/449 |
| 4,379,454 | 4/1983 | Campbell et al. | 424/449 |
| 4,460,372 | 7/1984 | Campbell et al. | 424/449 |
| 4,485,087 | 11/1984 | Otuska | 424/449 |
| 4,573,996 | 3/1986 | Kwintek et al. | 424/449 |
| 4,585,452 | 4/1986 | Sablotsky | 424/448 |
| 4,588,580 | 5/1986 | Gale et al. | 424/449 |
| 4,624,665 | 11/1986 | Nuwayser | 424/449 |
| 4,685,911 | 8/1987 | Konno et al. | 424/449 |
| 4,722,941 | 2/1988 | Eckert et al. | |
| 4,746,515 | 5/1988 | Cheng et al. | 424/449 |
| 4,751,087 | 6/1988 | Wick | 424/81 |

FOREIGN PATENT DOCUMENTS

| | | |
|---|---|---|
| 0062682 | 10/1982 | European Pat. Off. |
| 0156080 | 10/1985 | European Pat. Off. |
| 0272987 | 6/1988 | European Pat. Off. |
| 0279986 | 8/1988 | European Pat. Off. |
| 57-075917 | 5/1982 | Japan . |
| 1518683 | 7/1978 | United Kingdom . |
| 2086224 | 5/1982 | United Kingdom . |
| 2158355 | 12/1985 | United Kingdom . |
| 86902978.5 | 5/1986 | United Kingdom . |

*Primary Examiner*—Thurman K. Page
*Assistant Examiner*—Leon R. Horne
*Attorney, Agent, or Firm*—Gary L. Griswold; Walter N. Kirn; Douglas E. Reedich

[57] ABSTRACT

A pressure-sensitive adhesive sheet material for delivering estradiol to skin, the sheet material comprising a backing with a layer of a pressure-sensitive adhesive adjacent thereto, said pressure-sensitive adhesive layer comprising a pressure-sensitive adhesive polymer, two or more skin penetration-enhancing ingredients and estradiol. The sheet material is useful for systemic treatment of conditions associated with estradiol deficiency. Methods of using such adhesive sheet material are also described.

15 Claims, No Drawings

TRANSDERMAL ESTRADIOL DELIVERY SYSTEM

CROSS REFERENCE TO RELATED APPLICATION

This application is a continuation of Ser. No. 398,168 filed Aug. 24, 1989, now abandoned which is a continuation-in-part of application Ser. No. 322,895 filed Mar. 10, 1989, now abandoned which is a continuation-in-part of application Ser. No. 160,635 filed Feb. 26, 1988, now abandoned.

TECHNICAL FIELD

This invention relates to a pressure-sensitive adhesive sheet material containing estradiol in the adhesive portion of the sheet material. This invention further relates to a method of treating conditions associated with estradiol deficiency, such as osteoporosis and headaches, nausea, depression, hot flashes or other discomforts that often occur during menopause.

BACKGROUND OF THE INVENTION

Estradiol is a natural estrogen which has limited oral effectiveness because it is rapidly metabolized by the liver to estrone and its conjugates, giving rise to higher circulating levels of estrone than estradiol. In contrast, the skin metabolizes estradiol only to a small extent. Therefore, transdermal administration produces therapeutic serum levels of estradiol with lower circulating levels of estrone and estrone conjugates, and requires smaller total doses than does oral therapy. Since estradiol has a short half-life (about one hour), transdermal administration of estradiol allows a rapid decline in blood levels after a transdermal system is removed.

Estraderm ® is an estradiol transdermal system available from CIBA Pharmaceutical Company. This system comprises four layers: a transparent polyester film; a drug reservoir of estradiol and alcohol gel with hydroxypropyl cellulose; an ethylene-vinylacetate copolymer membrane; and an adhesive formulation of light mineral oil and polyisobutylene for adhering the patch to skin.

Japanese Application 57075917 describes the manufacture of a tacky tape for use with a variety of sex hormones including valeric acid-estradiol. The tape is prepared by (1) copolymerizing (a) 60-98 parts by weight of dodecyl methacrylate, (b) 2-40 pts. wt. of a functional monomer and (c) 0-40 pts. wt. of at least one short chain unsaturated monomer selected from vinyl acetate, an alkyl acrylate, and an alkyl methacrylate; (2) combining the drug with the copolymer; and (3) spreading the resulting composition onto base material.

U.S. Pat. No. 3,598,123 describes a medical bandage for use with a variety of drugs including estradiol. The bandage comprises: a backing member and a layer of pressure-sensitive adhesive containing a plurality of discrete microcapsules containing the drug. Acrylic adhesives are specifically mentioned.

U.S. Patent No. 4,460,372 describes a transdermal device comprising a backing and an adhesive layer, the adhesive layer containing both estradiol and a microencapsulated percutaneous absorption enhancer such as ethanol.

GB Application 2158355 describes an estradiol containing transdermal dosage form comprising: a solid non-polymeric gel; a mixture of propylene glycol and glycerin; the therapeutic agent dispersed in the solvent mixture; and a thin, flexible, non-polymeric matrix in planar form. The mixture of propylene glycol and glycerine is described as enhancing the skin penetration of the therapeutic agent.

U.S. Pat. Nos. 3,598,122, 4,379,452, 4,573,996, 4,585,454, 4,624,665, and U.S. Pat. No. 4,460,372 (also mentioned above) all describe estradiol transdermal patches which include layers in addition to a backing and an adhesive layer. For example, many of these patents describe patches comprising a backing, a drug reservoir layer; a semipermeable membrane; and an adhesive layer coated on the exterior surface of the semipermeable membrane. Said U.S. Pat. No. 4,573,996 discloses a variety of penetration enhancers in Col. 11, lines 44-68

European Application 86.902978 5 describes a transdermal nitroglycerin delivery system comprising a flexible backing and a pressure-sensitive adhesive coating comprising an acrylic polymer and nitroglycerin. The adhesive coating may also comprise a skin penetration enhancing combination comprising a fatty acid ester of a fatty acid such as ethyl oleate and glyceryl monolaurate.

U.S. Pat. No. 4,722,941 discloses transdermal and oral formulations employing a fatty acid of medium chain length and optionally a monoglyceride of a saturated or unsaturated fatty acid of about 6 to 18 carbon atoms to enhance drug absorption. The formulations may include a steroid.

Glyceryl monolaurate, isopropyl myristate and ethyl oleate are known enhancers for transdermal administration of medicaments.

BRIEF SUMMARY OF THE INVENTION

The present invention provides a novel adhesive-coated sheet material comprising:
(a) a flexible backing; and
(b) a pressure-sensitive adhesive-coating contiguously adhered to one surface of said backing and comprising a homogeneous mixture of:
  (i) an acrylic polymer comprising at least about 91 to 98 percent by weight of a hydrophobic monomeric acrylic or methacrylic acid ester of an alkyl alcohol based on the weight of all monomers in the polymer, the alkyl alcohol containing 4 to 10 carbon
  (ii) estradiol in an amount by weight of about 0.2 to 12 percent of the total weight of the adhesive coating; and
  (iii) a skin penetration enhancer combination comprising isopropyl myristate and glyceryl monolaurate in amounts of about 5 to 20 percent and about 1 to 6 percent by weight, respectively, based on the weight of the adhesive-coating with the relative amounts being selected so as to enhance the penetration of the estradiol through skin as compared to when the adhesive coating is free of said skin penetration enhancers;

the sheet material being suitable for substantially continuous transdermal delivery of estradiol to a subject over a prolonged period in an amount which is therapeutically effective for treating a condition associated with estradiol deficiency.

The present invention also provides a novel adhesive-coated sheet material comprising:
(a) a flexible backing; and
(b) a pressure-sensitive adhesive-coating contiguously adhered to one surface of said backing and comprising a homogeneous mixture of:

(i) an acrylic copolymer comprising (1) about 60 to 80 percent by weight of a hydrophobic monomeric acrylic or methacrylic acid ester of an alkyl alcohol based on the weight of all of the monomers in the copolymer, the alkyl alcohol containing 4 to 10 carbon atoms; (2) about 4 to 9 percent by weight based on the weight of all of the monomers in the copolymer of a reinforcing monomer selected from the group consisting of acrylic acid, methacrylic acid, an alkyl acrylate or methacrylate containing 1 to 3 carbon atoms in the alkyl group, acrylamide, methacrylamide, a lower diacetone acrylamide, and a N-vinyl-2-pyrrolidone; and (3) about 15 to 35 percent by weight of vinyl acetate based on the weight of all of the monomers in the copolymer;

(ii) estradiol in an amount by weight of about 0.2 to 12 percent of the total weight of the adhesive coating; and (iii) a skin penetration enhancer combination comprising isopropyl myristate and glyceryl monolaurate in amounts of about 5 to 20 percent and about 1 to 6 percent by weight, respectively, based on the weight of the adhesive coating, with the relative amounts being selected so as to enhance the penetration of the estradiol through skin as compared to when the adhesive coating is free of the skin penetration enhancers;

the sheet material being suitable for substantially continuous transdermal delivery of estradiol to a subject over a prolonged period in an amount which is therapeutically effective for treating a condition associated with estradiol deficiency.

In preferred embodiments of the invention, the skin penetration enhancer combination further contains ethyl oleate.

DETAILED DESCRIPTION OF THE INVENTION

The present invention relates to pressure-sensitive adhesive sheet materials comprising a backing and a layer of pressure-sensitive adhesive containing estradiol coated thereon. Further, this invention relates to a method of treating conditions associated with estradiol deficiency.

By "treating a condition associated with estradiol deficiency" as used in the instant specification and claims is meant administering a dose of estradiol in an amount and at a rate which eliminates or reduces the occurrence of one or more of the following conditions: osteoporosis, headaches, nausea, depression, hot flashes and any other discomfort that occurs during and after menopause. By "prolonged period" as used in the instant specification and claims is meant for a period of at least 12 hours.

The adhesives utilized in the practice of the invention should be substantially chemically inert to estradiol. Suitable acrylic adhesive polymers for use in one embodiment of the invention comprise in an amount of about 91 to 98 percent by weight, and preferably about 94 to 98 percent by weight, respectively, of all monomers in the polymer of a hydrophobic monomeric acrylic or methacrylic acid ester of an alkyl alcohol, the alkyl alcohol containing 4 to 10 carbon atoms. Examples of suitable monomers are those discussed below in connection with the "A Monomer". These adhesive polymers further comprise minor amounts of other monomers such as the "B Monomers" listed below.

Preferred adhesives are acrylic pressure-sensitive adhesive copolymers comprising A and B monomers as follows: Monomer A is a hydrophobic monomeric acrylic or methacrylic acid ester of an alkyl alcohol, the alkyl alcohol containing 4 to 10 carbon atoms, preferably 6 to 10 carbon atoms, more preferably 6 to 8 carbon atoms, and most preferably 8 carbon atoms. Examples of suitable A monomers are n-butyl, n-pentyl, n-hexyl, isoheptyl, n-nonyl, n-decyl, isohexyl, 2-ethyloctyl, isooctyl and 2-ethylhexyl acrylates. The most preferred A monomer is isooctyl acrylate.

Monomer B is a reinforcing monomer selected from the group consisting of acrylic acid; methacrylic acid; alkyl acrylates and methacrylates containing 1 to 3 carbon atoms in the alkyl group; acrylamide; methacrylamide; lower alkyl-substituted acrylamides (i.e. the alkyl group containing 1 to 4 carbon atoms) such as tertiary-butyl acrylamide; diacetone acrylamide; N-vinyl-2-pyrrolidone; vinyl ethers such as vinyl tertiary-butyl ether; substituted ethylenes such as derivatives of maleic anhydride, dimethyl itaconate and monoethyl formate and vinyl perfluoro-n-butyrate. The preferred B monomers are acrylic acid, methacrylic acid, the above-described alkyl acrylates and methacrylates, acrylamide, methacrylamide, and the above-described lower alkyl substituted acrylamides. The most preferred B monomer is acrylamide.

The B monomer in such a copolymer is present in the pressure-sensitive adhesive copolymer in an amount by weight of about 2 to 9 percent by weight, and preferably about 2 to 6 percent by weight of the weight of all monomers in the copolymer.

In another embodiment of the invention, the acrylic copolymer comprises about 60 to 80 percent by weight (and preferably about 70 to 80 percent by weight) of the above-mentioned hydrophobic monomeric acrylic or methacrylic acid ester of an alkyl alcohol based on the weight of the monomers in the copolymer; about 4 to 9 percent by weight based on the weight of all monomers in the copolymer of a reinforcing monomer selected from the group consisting of acrylic acid, methacrylic acid, an alkyl acrylate or methacrylate containing 1 to 3 carbon atoms in the alkyl group, acrylamide, methacrylamide, a lower alkyl-substituted acrylamide, diacetone acrylamide and N-vinyl-2-pyrrolidone; and about 15 to 35 percent by weight (and preferably about 15 to 25 percent by weight) of vinyl acetate based on the weight of all monomers in the copolymer. In this embodiment the preferred acrylic or methacrylic acid ester is isooctyl acrylate and the preferred reinforcing monomer is acrylamide. The adhesive copolymers of the above type are known and their method of preparation is well known to those skilled in the art, having been described for example, in U.S. Pat. RE 24,906 of Ulrich, incorporated herein by reference. Since the pressure-sensitive adhesives described above are inherently rubbery and tacky and are suitably heat and light stable, there is no need to add tackifiers or stabilizers. However, such may be added if desired. The polymerization may be carried out using a free radical initiator. Examples of such are organic peroxides such as benzoyl peroxide and azo compounds such as 2,2'-azobis(2,4-dimethylpentanenitrile) which is available under the trade designation "Vazo 52" from DuPont.

The estradiol is present in the adhesive in a pharmaceutically effective amount. Generally this amount will be from about 0.2 to 12 percent by weight of the total weight of the pressure-sensitive adhesive layer of the sheet material, and will preferably be about 1 to 5 percent by weight. The most preferred is an amount of about 2 to 3.5 percent by weight.

It has been found that the addition of certain skin penetration enhancers significantly enhances the penetration of estradiol in vitro when this phenomena is measured using the hairless mouse skin model as described hereinbelow. Hence, the adhesive sheet material of the invention has an adhesive coating comprising a combination of two or more ingredients in an amount effective to enhance the penetration of estradiol through skin as compared to when said adhesive coating is free of the skin penetration enhancers.

More specifically, the adhesive-coating comprises isopropyl myristate and glyceryl monolaurate as penetration enhancers. In a preferred embodiment, the adhesive-coating additionally comprises ethyl oleate.

The isopropyl myristate will generally be present in an amount of about 5 to 20 percent by weight, and preferably about 5 to 15 percent by weight, of the total weight of the adhesive coating and the glyceryl monolaurate will generally be present in an amount of about 1 to 6 percent, and preferably about 2 to 4 percent by weight. When the adhesive-coating additionally contains ethyl oleate, ethyl oleate will generally be present in an amount by weight of about 4 to 18 percent, and preferably about 5 to 15 percent, based on the weight of the adhesive coating. When ethyl oleate is present the total weight of ethyl oleate and isopropyl myristate will not exceed about 30 percent by weight of the adhesive-coating.

A suitable glyceryl monolaurate is that commercially available from Lauricidin Inc. (Monroe, Michigan) under the trade designation Lauricidin (distilled (monoglyceride). The sheet material comprises a flexible backing. The backing may be occlusive, non-occlusive or a breathable film. The backing may be any of the normal materials for pressure-sensitive adhesive tapes such as polyethylene, particularly low-density polyethylene, linear low density polyethylene, high density polyethylene, randomly-oriented nylon fibers, polypropylene, ethylene-vinylacetate copolymer, polyurethane, rayon and the like. The backing should be substantially non-reactive with estradiol.

The presently preferred backing is low density polyethylene. Low density polyethylene backings provide an excellent barrier to loss of estradiol when used with the adhesive formulations of the invention, including those formulations which contain a skin penetration enhancer.

Backings which are layered such as polyethylene-aluminum-polyethylene composites are also suitable.

Although animal skins are known to give significant quantitative differences in drug penetration rates versus human skin, the rank order correlation is generally observed with various drugs (M. J. Bartek and J. A. LaBudde in "Animal Modes in Dermatology", H. Maibach, Ed. Churchill Livingstone, New York, 1975, pp. 103-119). Hairless mouse skin has been recommended as a readily available animal skin for use in diffusion cells with steroids and small molecules (R. B. Stoughton, Arch. Derm., 99, 753 (1969), J. L. Cohen and R. B. Stoughton, J. Invest. Derm., 62, 507 (1974), R. B. Stoughton in "Animal Modes in Dermatology", H. Maibach, Ed., Churchill Livingstone, NY, 1975, pp. 121-131).

In the specific test procedure used herein, skin removed from female hairless mice (available from Jackson Laboratory, Strain HRS/J, age 2–5 months) is used. It is maintained on ice until used. The mouse skin is cut in half and each half is mounted, or the skin is used whole, on a diffusion cell of the type shown in the drawing. The cell is modeled after those described in the literature (e.g. J. L. Cohen, R. B. Stoughton, J. Invest. Derm. 62 507 (1974) and R. B. Stoughton, Arch. Derm. 99, 753 (1964). As shown in the figure, the mouse or human skin (20) is mounted epidermal side up between the upper and lower portions of the cell (21) and (22), which are held together by means of a ball joint clamp (23). The cell below the skin is filled with 30% N-methyl-2-pyrrolidone in water to act as the "acceptor" fluid thus maintaining an adequate "sink" receptor. The acceptor fluid is stirred using a magnetic stirring bar (24) and a magnetic stirrer (not illustrated). The sampling port (25) is stoppered except when in use.

A known amount of a formulation to be evaluated is applied to the epidermal (upper) side of the skin in a uniform layer as follows: The desired area and weight of a sheet material formulation is accurately determined so that the amount of adhesive applied to the cell can be accurately determined. The sheet material is applied to the skin already mounted on the diffusion cell and pressed to cause uniform contact to the skin.

The cell is then placed in a constant temperature (31 to 33° C.) constant humidity chamber (generally maintained at a humidity between 40 and 50%, preferably about 50%) and kept there throughout the experiment. The chamber utilizes a heat exchanger coupled to a constant temperature bath, with a fan to circulate air. A saturated calcium nitrate solution is used to maintain the humidity. The acceptor fluid is stirred by means of a magnetic stirring bar throughout the experiment to assure a uniform sample and a reduced aqueous diffusion layer on the dermal side of the skin. The acceptor fluid is removed at specified time intervals and fresh fluid is immediately added to replace the withdrawn fluid. The withdrawn aliquots are analyzed for drug content by conventional high pressure liquid chromatograpy and the cumulative amount of the drug penetrating the skin is calculated. Plots of the cumulative drug penetration as a function of time give a profile of the drug flux measured in $microg/cm^2/hour$.

The use of other skin such as human skin in the above apparatus has confirmed the utility of the formulations of the invention.

The sheet materials of the present invention are preferably prepared by combining adhesive, estradiol and the skin penetration enhancers with an organic solvent. Preferred organic solvents are methanol and ethyl acetate. The total solids content will be in the range of about 15 to 40% and preferably about 20 to 35%. The resulting mixture is shaken at a high speed until a homogeneous solution is obtained and then allowed to stand to dissipate air bubbles. The resulting formulation may be wet cast or coated by wet-cast or knife coating techniques to provide a predetermined uniform thickness of the wet adhesive formulation onto a suitable release liner. This sheet is then dried and laminated onto a backing material using conventional methods. Suitable release liners are known silicone-type release liners such as that available under the trade designation Daubert 164, from Daubert Co. which are coated onto polyester film. The adhesive coated sheet material of the invention may be in the form of a tape, a patch, a sheet, a dressing or other forms known to the art as will be apparent to one skilled in the art. Preferably, the adhesive coated sheet material will contain about 0.2 to 7.0 mg, and preferably about 1.0 to 2.0 mg, of estradiol per 5 cm² of the sheet material. Further, the sheet material will generally be about 1 to 40 cm², and preferably 10 to 30 cm², in dimension.

Generally, a transdermal patch of the invention will be applied to the skin of a mammal (preferably a human) and will be replaced with a fresh patch as required to maintain the therapeutic effect. Those skilled in the art may easily determine the frequency at which the patches of the invention should be replaced to achieve the desired therapeutic effect. The following examples are provided to illustrate the invention, but are not intended to be limiting thereof. Parts and percentages are by weight unless otherwise specified. Flux rates are expressed in units of micrograms of estradiol per cm² for the time period specified in the example. Each result represents the average value of several (e.g., 3 to 5) independent determinations.

Inherent Viscosity Measurement

In the examples which follow, it is useful to refer to the molecular weight of the adhesive polymer used in the adhesive formulations. The comparative molecular weights are determined by measuring the viscosity of dilute solutions of the adhesives prepared according to these teachings.

The inherent viscosity values which are reported in the examples which follow were obtained by the conventional method used by those skilled in the art. The measurement of the viscosity of dilute solutions of the adhesive, when compared to controls run under the same conditions, clearly demonstrates the relative molecular weights. It is the comparative values which are significant and absolute figures are not required. In the examples, the inherent viscosity values were obtained using a Cannon-Fenske #50 viscometer in a water bath controlled at 25° C. to measure the flow time of 10 ml of a polymer solution. The examples and controls being run for comparison were run under identical conditions. The test procedure followed and the apparatus used are explained in detail in the *Textbook of Polymer Science*, F. W. Billmeyer, Wiley-Interscience, 2nd Edition, 1971 under: Polymer chains and their characterization, D. Solution Viscosity and Molecular Size, pages 84 and 85.

Preparation of Adhesive Copolymers

Part A. Preparation of Isooctyl Acrylate: Acrylamide (94:6) Copolymer

To a quart narrow-mouth glass bottle were added: 127.84 g. isooctyl acrylate, 8.6 g. acrylamide, 0.41 g. benzoyl peroxide, 237.6 g. ethyl acetate and 26.4 g. methyl alcohol. The solution was purged for two minutes with nitrogen at a flow rate of one liter per minute. The bottle was sealed and placed in a rotating water bath at 55° C. for twenty four hours to effect essentially complete polymerization. The polymer was diluted with ethyl acetate/methyl alcohol (90/10) to 28.4% solids and had a measured inherent viscosity of 1.02 dl/g. in ethyl acetate at a concentration of 0.15 g/dl. Its Brookfield viscosity was 9,120 centipoise.

Part B. Preparation of Isooctyl Acrylate: Acrylamide (95 5) Copolymer

The procedures above were repeated, this time employing 152.00 g. isooctyl acrylate, 8.0 g. acrylamide, 0.48 g. benzoyl peroxide, 216.0 g. ethyl acetate and 24.0 g. methyl alcohol. The resulting polymer was diluted with the ethyl acetate/methyl alcohol mixture to 29.38% solids. The polymer had a measured inherent viscosity of 1.32 dl/g in ethyl acetate at a concentration of 0.15 g/dl. Its Brookfield viscosity was 9,900 centipoise.

A 25–30 percent solids solution of the above isooctyl acrylate:acrylamide (94:6) adhesive copolymer or the above isooctyl acrylate: acrylamide (95:5) adhesive copolymer in ethyl acetate/methanol (90:10) was coated onto a 2-sided release liner using a knife-coater and coating at 20 mils in thickness. The adhesive-coated laminate was dried first at 180° F. for 3 minutes and then at 240° F. for 3 minutes. The dried adhesive coating was then stripped off the release liner and placed into a small glass bottle. The foregoing procedure results in a reduction of the amount of residual monomer which may be contained in the adhesive copolymer.

Part C. Preparation of Isooctyl Acrylate: Acrylamide: Vinyl Acetate (75:5:20) Copolymer The procedures above were repeated this time employing 120.0 g. isooctyl acrylate, 8.0 g. acrylamide, 32.0 g. vinyl acetate, 0.32 g. benzoyl peroxide, 216.0 g. ethyl acetate and 24.0 g. methyl alcohol. The resulting polymer was diluted with the ethyl acetate/methyl alcohol mixture to 21.52% solids. The adhesive polymer had a measured inherent viscosity of 1.40 dl/g in ethyl acetate at a concentration of 0.15 g/dl. Its Brookfield viscosity was 2,300 centipoise.

Part D. Preparation of Isooctyl Acrylate: Acrylamide: Vinyl Acetate (75:5:20) Copolymer A master batch was prepared by combining 621.0 g of isooctyl acrylate, 41.4 g of acrylamide, 165.6 g of vinyl acetate, 1.656 g of 2,2'-azobis(2,4-dimethylpentanenitrile) (available from the DuPont Company under the tradename Vazo 52), 884.52 g of ethyl acetate and 87.48 g of methanol. A 400 g portion of the resulting solution was placed in an amber quart bottle. The bottle was purged for two minutes with nitrogen at a flow rate of one liter per minute. The bottle was sealed and placed in a rotating water bath at 45° C. for twenty-four hours to effect essentially complete polymerization. The copolymer was diluted with 250 g of ethyl acetate/methanol (90/10) to 26.05% solids and had a measured inherent viscosity of 1.27 dl/g in ethyl acetate at a concentration of 0.15 g/dl. Its Brookfield viscosity was 5580 centipoise.

Part E. Preparation of Isooctyl Acrylate: Acrylamide (95:5) Copolymer

The procedures above were repeated this time employing 803.7 g of isooctyl acrylate, 42.3 g of acrylamide, 1.69 g of 2,2'-azobis(2,4-dimethylpentanenitrile), 858.6 g of ethyl acetate and 95.4 g of methanol. The resulting copolymer was diluted with ethyl acetate/methanol (90/10) to 28.37% solids. The adhesive copolymer had a measured inherent viscosity of 1.35 dl/g in ethyl acetate at a concentration of 0.15 g/dl. Its Brookfield viscosity was 12,000 centipoise.

Part F. Preparation of Isooctyl Acrylate: Acrylamide (94:6) Copolymer

The procedures above were repeated this time employing 782.55 g of isooctyl acrylate, 49.95 g of acrylamide, 1.665 g of 2,2'-azobis(2,4-dimethylpentanenitrile), 1275.75 g of ethyl acetate and 141.75 g of methanol. The resulting copolymer was diluted with ethyl acetate/methanol (90/10) to 26.86% solids and had a measured inherent viscosity of 1.00 dl/g in ethyl acetate at a concentration of 0.15 g/dl. The Brookfield viscosity was 2,320 centipoise.

EXAMPLE 1

A mixture of 200.62 g of 95:5 isooctyl acrylate:acrylamide adhesive copolymer (from Part B above), 33.75 g of isopropyl myristate, 8.75 g of glyceryl monolaurate, 6.88 g of estradiol USP, 525.00 g of ethyl acetate and 58.33 g of methanol was placed in a jar. The jar was placed on a platform shaker and shaken for about 18 hours. The formulation was allowed to stand until all the air bubbles had dissipated. The formulation was coated at a thickness of 0.022 inches onto a silicone coated 5 mil liner. The laminate was oven dried for 2 minutes at 125° F., for 2 minutes at 185° F. and for 2 minutes at 235° F. (too vigorous conditions for drying may result in loss of a major amount of the isopropyl myristate). The resulting adhesive coating contained 80.25 percent 95:5 isooctyl acrylate:acrylamide adhesive copolymer, 13.50 percent isopropyl myristrate, 3.50 percent glyceryl monolaurate and 2.75 percent estradiol. The material was allowed to cool and was then laminated onto the corona treated surface of a 3 mil low density polyethylene backing. The laminate was die cut into 2 cm$^2$ patches. Penetration through hairless mouse skin was measured using the diffusion apparatus and method described above. The acceptor fluid was 30% N-methyl-2-pyrrolidone in water. Three independent determinations were carried out. The average penetration in 124 hours was 74 micrograms/cm$^2$.

EXAMPLE 2-4

Using the general method of Example 1 the formulations shown in Table 1 were prepared and the penetration through hairless mouse skin measured. The acceptor fluid was 30% N-methyl-2-pyrrolidone in water. Patches which measured 2 cm$^2$ were employed.

TABLE 1

| Formulation | Penetration Micrograms/cm$^2$ in 24 hrs |
| --- | --- |
| 2.75% estradiol | 75 |
| 3.50% glyceryl monolaurate | |
| 13.50% isopropyl myristate | |
| 80.25% isooctyl acrylate: acrylamide copolymer (94:6) (from Part A above) | |
| 2.75% estradiol | 87 |
| 3.50% glyceryl monolaurate | |
| 10.60% isopropyl myristate | |
| 5.30% ethyl oleate | |
| 77.85% isooctyl acrylate: acrylamide copolymer (95:5) (from Part B above) | |
| 2.75% estradiol | 87 |
| 3.50% glyceryl monolaurate | |
| 10.60% isopropyl myristate | |
| 5.30% ethyl oleate | |
| 77.85% isooctyl acrylate: acrylamide copolymer (94:6) (from Part A above) | |

EXAMPLE 5

A mixture of 23.31 g of isooctyl acrylate:acrylamide:-vinyl acetate adhesive copolymer (from Part C above), 21.66% solids in 90L10 ethyl acetate:methanol, 0.184 g of estradiol USP, 0.8035 g of isopropyl myristate, 0.2402 g of glyceryl monolaurate and 0.4130 g of ethyl oleate was placed in a jar. The jar was placed on a platform shaker and shaken for about 20 hours. The formulation was allowed to stand until air bubbles had dissipated. The formulation was coated at a thickness of 0.022 inches onto a 5 mil Daubert 164Z release liner. The laminate was oven dried for 4 min. at 125° F., for 2 minutes at 185° F. and for 1 minute at 225° F. The resulting adhesive coating contained 75.5 percent 75:5:20 isooctyl acrylate:acrylamide:vinyl acetate adhesive copolymer, 2.75 percent estradiol, 12.0 percent isopropyl myristate, 6.2 percent ethyl oleate and 3.6 percent glyceryl monolaurate. The material was then laminated onto the corona treated surface of a 3 mil low density polyethylene film and die cut into 5.07 cm$^2$ patches Penetration through hairless mouse skin was measured. The acceptor fluid was 30% N-methyl-2-pyrrolidone in water. Three independent determinations were made. The average amount penetrating in 24 hours was 84 micrograms/cm$^2$.

EXAMPLE 6-8

Using the general method of Example 5 the formulations shown in Table 2 were prepared and the penetration through hairless mouse skin measured. The adhesive used was an isooctyl acrylate:acrylamide:vinyl acetate 75:5:20 copolymer (from Part C above). The acceptor fluid was 30% N-methyl-2-pyrrolidone in water. Patches measuring 5.07 cm$^2$ were employed.

TABLE 2

| Formulation | Penetration Micrograms/cm$^2$ in 24 hrs |
| --- | --- |
| 2.75% estradiol | 112 |
| 14.0% isopropyl myristate | |
| 7.4% ethyl oleate | |
| 3.5% glyceryl monolaurate | |
| 72.7% adhesive | |
| 2.74% estradiol | 98 |
| 6.1% isopropyl myristate | |
| 12.4% ethyl oleate | |
| 3.5% glyceryl monolaurate | |
| 75.2% adhesive | |
| 2.76% estradiol | 130 |
| 7.0% isopropyl myristate | |
| 14.1% ethyl oleate | |
| 3.5% glyceryl monolaurate | |
| 72.6% adhesive | |

EXAMPLE 9

A mixture of 481.50 g of 95:5 isooctyl acrylate:acrylamide adhesive copolymer (from Part E above), 81.00 g of isopropyl myristate, 21.00 g of glyceryl monolaurate, 16.50 g of estradiol USP, 1800 g of ethyl acetate and 200 g of methanol was placed in a jar. The jar was tightly sealed then placed on a linear platform shaker and shaken for about 19 hours. The resulting formulation was allowed to stand until the air bubbles had dissipated. The formulation was coated at a thickness of 25 mils onto a silcone coated polyester 4 mil liner. The laminate was dried for 2 minutes at 125° F., for 2 minutes at 185° F. and for 2 minutes at 235° F. The resulting adhesive coating contained 80.25 percent 95:5 isooctyl acrylate:acrylamide adhesive copolymer, 13.50 percent isopropyl myristate, 3.50 percent glyceryl monolaurate and 2.75 percent estradiol. The material was then laminated onto the corona treated surface of a 3 mil low density polyethylene backing. The laminate was die cut into 5 cm$^2$ patches. Penetration through hairless mouse skin was measured using the diffusion apparatus and method described above. The acceptor fluid was 30% N-methyl-2-pyrrolidone in water. Three independent determinations were carried out. The penetration rate was 3.81 micrograms/cm²/hour.

EXAMPLE 10

A mixture of 467.10 g of 95:5 isooctyl acrylate:acrylamide adhesive copolymer (from Part E above), 63.60 g of isopropyl myristate, 31.80 g of ethyl oleate, 21.00 g of glyceryl monolaurate, 16.50 g of estradiol USP, 1388.6 g of ethyl acetate and 154.3 g of methanol was placed in a jar. The jar was tightly sealed, placed on a linear platform shaker and shaken for about 24 hours. The resulting formulation was allowed to stand until the air bubbles had dissipated. The formulation was coated at a thickness of 22 mils onto a silicone coated 4 mil polyester release liner. The laminate was dried for 2 minutes at 125° F., for 2 minutes at 185° F. and for 2 minutes at 235° F. The resulting adhesive coating contained 77.85 percent 95:5 isooctyl acrylate:acrylamide adhesive copolymer, 10.60 percent isopropyl myristate, 5.30 percent ethyl oleate, 3.50 percent glyceryl monolaurate and 2.75 percent estradiol. The material was laminated onto the corona treated surface of a 3 mil low density polyethylene backing. The laminate was die cut into 5 cm² patches Penetration through hairless mouse skin was measured using the diffusion apparatus and method described above. The acceptor fluid was 30% N-methyl-2-pyrrolidone. Three independent determinations were carried out. The penetration rate was 4.52 micrograms/cm²/hour.

EXAMPLE 11

Using the general method of Example 10 a formulation containing 80.25 percent 94:6 isooctyl acrylate:acrylamide adhesive copolymer (from Part F above), 13.50 percent isopropyl myristate, 3.50 percent glyceryl monolaurate and 2.75 percent estradiol was prepared. The laminate was die cut into 5 cm² patches. Penetration through hairless mouse skin was measured using the apparatus and method described above. The acceptor fluid was 30% N-methyl-2-pyrrolidone. Three independent determinations were carried out. The penetration rate was 2.38 micrograms/cm²/hour.

EXAMPLE 12

A mixture of 1995.8 g of isooctyl acrylate:acrylamide:vinyl acetate adhesive copolymer (from Part D above), 24.7% solids in 90:10 ethyl acetate:methanol, 94.9 g of ethyl oleate, 47.4 g of isopropyl myristate, 23.7 g of glyceryl monolaurate and 9.3 g of estradiol was placed in a jar. The jar was sealed then placed on a linear platform shaker and shaken for about 17 hours. The formulation was allowed to stand until air bubbles had dissipated. The formulation was coated at a thickness of about 19.5 mils onto a 4 mil release liner. The laminate was dried for 5 minutes at 125° F., for 2 minutes at 185° F. and for 2 minutes at 235° F. The resulting adhesive coating contained 72.65% 75:5:20 isooctyl acrylate:acrylamide:vinyl acetate adhesive copolymer, 14.0% ethyl oleate, 7.0% isopropyl myristate, 3.5% glyceryl monolaurate and 2.85% estradiol. The material was then laminated onto the corona treated surface of 3 mil low density polyethylene film and die cut into 5.07 cm² patches. Penetration through hairless mouse skin was measured using the diffusion apparatus and method described above. The acceptor fluid was 30% N-methyl-2-pyrrolidone in water. Five independent determinations were carried out. The penetration rate was 6.3 micrograms/cm²/hour.

What is claimed is:

1. An adhesive-coated sheet material comprising:
   (a) a flexible backing; and
   (b) a pressure-sensitive adhesive coating contiguously adhered to one surface of said backing and comprising a homogeneous mixture of:
      (i) an acrylic copolymer comprising about 91 to 98 percent by weight of a hydrophobic monomeric acrylic or methacrylic acid ester of an alkyl alcohol based on the weight of all monomers in said copolymer, the alkyl alcohol containing 4 to 10 carbon atoms and 2 to 9 percent by weight of a reinforcing monomer selected from the group consisting of acrylic acid; methacrylic acid; an alkyl acrylate or methacrylate containing 1 to 3 carbon atoms in the alkyl group acrylamide; methacrylamide; a lower alkyl-substituted acrylamide; diacetone acrylamide; N-vinyl-2-pyrrolidone; a vinyl ether; vinyl ester and a substituted ethylene;
      (ii) estradiol in an amount by weight of about 0.2 to 12 percent of the total weight of said adhesive coating; and
      (iii) a skin penetration enhancer combination comprising isopropyl myristate and glyceryl monolaurate in amounts of about 5 to 20 percent and about 1 to 6 percent by weight, respectively, based on the weight of said adhesive-coating, with the relative amounts being selected so as to enhance the penetration of said estradiol through skin as compared to when said adhesive coating is free of said skin penetration enhancers;
said sheet material being further characterized in that over a prolonged period it adheres suitably to skin and provides for substantially continuous transdermal delivery of estradiol to a subject in an amount which is therapeutically effective for treating a condition associated with estradiol deficiency.

2. An adhesive-coated sheet material according to claim 1, wherein said adhesive copolymer comprises said acrylic of methacrylic acid ester in an amount of about 94 to 98 percent by weight.

3. An adhesive-coated sheet material according to claim 2, wherein said adhesive copolymer comprises isooctyl acrylate as the A monomer and acrylamide as the B monomer.

4. An adhesive-coated sheet material according to claim 1, wherein the amount of estradiol in said adhesive coating is about 1 to 5 percent by weight of said adhesive coating.

5. An adhesive-coated sheet material according to claim 1, wherein the amount of estradiol in said adhesive coating is about 2 to 3.5 percent by weight of said adhesive coating.

6. An adhesive-coated sheet material according to claim 1, wherein said isopropyl myristate and glyceryl monolaurate are present in amounts by weight of about 5 to 15 percent and 2 to 4 percent, respectively, based on the weight said adhesive coating.

7. An adhesive-coated sheet material according to claim 1, wherein said skin penetration enhancer combination further comprises about 4 to 18 percent by weight of ethyl oleate based on the weight of said adhesive coating, and wherein the total amount by weight of isopropyl myristate and ethyl oleate is less than about 30 percent based on the weight of said adhesive coating.

8. A method of treating a condition associated with estradiol deficiency wherein an adhesive-coated sheet material according to claim 1 is applied and adhered to the skin of a mammal to permit systemic delivery of estradiol to said mammal.

9. An adhesive-coated sheet material comprising:
(a) a flexible backing; and
(b) a pressure-sensitive adhesive coating contiguously adhered to one surface of said backing and comprising a homogeneous mixture of:
(i) an acrylic copolymer comprising (1) about 60 to 80 percent by weight of a hydrophobic monomeric acrylic or methacrylic acid ester of an alkyl alcohol based on the weight of all monomers in said copolymer, the alkyl alcohol containing 4 to 10 carbon atoms; (2) about 4 to 9 percent by weight based on the weight of all monomers in said copolymer of a reinforcing monomer selected from the group consisting of acrylic acid, methacrylic acid, an alkyl acrylate or methacrylate containing 1 to 3 carbon atoms in the alkyl group, acrylamide, methacrylamide, a lower alkyl-substituted acrylamide, diacetone acrylamide, and N-vinyl-2-pyrrolidone; and (3) about 15 to 35 percent by weight of vinyl acetate based on the weight of all monomers in said copolymer;
(ii) estradiol in an amount by weight of about 0.2 to 12 percent of the total weight of said adhesive coating; and
(iii) a skin penetration enhancer combination comprising isopropyl myristate and glyceryl monolaurate in amounts of about 5 to 20 percent and about 1 to 6 percent by weight, respectively, based on the weight of said adhesive coating with the relative amounts being selected so as to enhance the penetration of said estradiol through skin as compared to when said adhesive coating is free of said skin penetration enhancers; said sheet material being further characterized in that over a prolonged period it adheres suitably to skin and provides substantially continuous transdermal delivery of estradiol to a subject in an amount which is therapeutically effective for treating a condition associated with estradiol deficiency.

10. An adhesive-coated sheet material according to claim 9, wherein said ester is isooctyl acrylate and said reinforcing monomer is acrylamide.

11. An adhesive-coated sheet material according to claim 9, wherein the amount of estradiol in said adhesive coating is about 1 to 5 percent by weight of said adhesive coating.

12. An adhesive-coated sheet material according to claim 9, wherein the amount of estradiol in said adhesive coating is about 2 to 3.5 percent by weight of said adhesive coating.

13. An adhesive-coated sheet material according to claim 10, wherein said isopropyl myristate and glyceryl monolaurate are present in amounts by weight of about 5 to 15 percent and 2 to 4 percent, respectively, based on the weight of said adhesive coating.

14. An adhesive-coated sheet material according to claim 9, wherein said skin penetration enhancer combination further comprises about 4 to 18% by weight of ethyl oleate based on the weight of said adhesive coating, and wherein the total amount by weight of isopropyl myristate and ethyl oleate is less than about 30% by weight based on the weight of said adhesive coating.

15. A method of treating a condition associated with estradiol deficiency wherein an adhesive-coated sheet material according to claim 9 is applied and adhered to the skin of a mammal to permit systemic delivery of estradiol to said mammal.

* * * * *

UNITED STATES PATENT AND TRADEMARK OFFICE
CERTIFICATE OF CORRECTION

PATENT NO. : 5,223,261
DATED : June 29, 1993
INVENTOR(S) : Gregory R. Nelson et al.

It is certified that error appears in the above-indentified patent and that said Letters Patent is hereby corrected as shown below:

Col. 2, line 45, after "carbon" insert --atoms;--.
Col. 3, line 12, after "lower" insert --alkyl-substituted acrylamide,--.
Col. 9, line 33, "124" should read --24--.
Col. 9, line 34, "EXAMPLE" should read --EXAMPLES--.
Col. 9, line 66, "90L10" should read --90:10--.
Col. 10, line 14, "patches" should read --patches.--.
Col. 11, line 26, "patches" should read --patches.--.
Col. 11, line 51, "9.3 g" should read --19.3 g--.
Col. 12, line 18, "group" should read --group;--.

Signed and Sealed this

Thirteenth Day of December, 1994

Attest:

BRUCE LEHMAN

Attesting Officer   Commissioner of Patents and Trademarks